(12) United States Patent
Resca

(10) Patent No.: US 8,414,544 B2
(45) Date of Patent: Apr. 9, 2013

(54) BRONCHOTRACHEAL ACCESS VALVE FOR A BRONCHOASPIRATION APPARATUS

(75) Inventor: Daniele Resca, San Felice sul Panaro (IT)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

(21) Appl. No.: 11/917,339

(22) PCT Filed: Jun. 12, 2006

(86) PCT No.: PCT/EP2006/005623
§ 371 (c)(1),
(2), (4) Date: Dec. 12, 2007

(87) PCT Pub. No.: WO2006/133882
PCT Pub. Date: Dec. 21, 2006

(65) Prior Publication Data
US 2009/0287151 A1  Nov. 19, 2009

(30) Foreign Application Priority Data
Jun. 15, 2005 (IT) ................ B02005A0404

(51) Int. Cl.
*A61M 5/00* (2006.01)
*A61M 1/00* (2006.01)

(52) U.S. Cl.
USPC .......................................... 604/248; 604/32

(58) Field of Classification Search ................ 604/119, 604/118; 128/207.16, 207.15
See application file for complete search history.

(56) References Cited

U.S. PATENT DOCUMENTS

| | | | |
|---|---|---|---|
| 3,937,220 A | 2/1976 | Coyne | 128/276 |
| 3,991,762 A | 11/1976 | Radford | 128/276 |
| 4,569,344 A | 2/1986 | Palmer | 128/207.16 |
| 4,638,539 A | 1/1987 | Palmer | 29/469 |
| 4,696,296 A | 9/1987 | Palmer | 128/207.16 |
| 4,805,611 A | 2/1989 | Hodgkins | 128/207.14 |
| 4,825,859 A | 5/1989 | Lambert | 128/202.16 |
| 4,834,726 A | 5/1989 | Lambert | 604/281 |
| 4,836,199 A | 6/1989 | Palmer | 128/207.16 |
| 4,850,350 A | 7/1989 | Jackson | 128/207.16 |
| 4,872,579 A | 10/1989 | Palmer | 128/205.19 |
| 4,938,741 A | 7/1990 | Lambert | 604/19 |
| 4,967,743 A | 11/1990 | Lambert | 128/202.16 |
| 4,981,466 A | 1/1991 | Lumbert | 604/19 |

(Continued)

FOREIGN PATENT DOCUMENTS

| | | |
|---|---|---|
| DE | 3538033 | 4/1987 |
| EP | 1208865 | 5/2002 |

(Continued)

OTHER PUBLICATIONS

International Search Report and Written Opinion, PCT/EP2006/005623, pp. 10, Oct. 23, 2006.

*Primary Examiner* — Nicholas Lucchesi
*Assistant Examiner* — Weng Lee

(57) ABSTRACT

A bronchotracheal access valve for a bronchoaspiration apparatus. The valve is characterized in that the rotation of a second member in a given direction with respect to a first member moves the valve from a configuration in which a conduit communicates hydraulically with a sleeve, to a configuration in which the conduit communicates hydraulically with a flush conduit via a duct and a channel to flush an end portion of a catheter.

15 Claims, 4 Drawing Sheets

U.S. PATENT DOCUMENTS

| | | | | |
|---|---|---|---|---|
| 4,998,915 A | | 3/1991 | Hannah | 604/73 |
| 5,025,806 A | | 6/1991 | Palmer et al. | 128/203.12 |
| 5,029,580 A | | 7/1991 | Radford et al. | 128/207.14 |
| 5,059,208 A | * | 10/1991 | Coe et al. | 623/9 |
| 5,060,646 A | | 10/1991 | Page | 128/207.14 |
| 5,065,754 A | | 11/1991 | Jensen | 128/200.26 |
| 5,073,164 A | | 12/1991 | Hollister et al. | 604/43 |
| 5,083,561 A | | 1/1992 | Russo | 128/207.16 |
| 5,107,829 A | | 4/1992 | Lambert | 128/202.16 |
| 5,125,893 A | | 6/1992 | Dryden | 604/54 |
| 5,133,345 A | | 7/1992 | Lambert | 128/202.16 |
| 5,134,996 A | | 8/1992 | Bell | 128/207.14 |
| 5,139,018 A | | 8/1992 | Brodsky et al. | 128/207.14 |
| 5,215,522 A | | 6/1993 | Page et al. | 604/33 |
| 5,220,916 A | | 6/1993 | Russo | 128/207.16 |
| 5,246,012 A | | 9/1993 | Strickland | 128/768 |
| 5,254,098 A | | 10/1993 | Ulrich et al. | 604/171 |
| 5,255,676 A | | 10/1993 | Russo | 128/207.14 |
| 5,269,756 A | | 12/1993 | Dryden | 604/54 |
| 5,277,177 A | | 1/1994 | Page et al. | 128/200.26 |
| 5,309,902 A | | 5/1994 | Kee et al. | 128/202.27 |
| 5,325,850 A | | 7/1994 | Ulrich et al. | 128/200.26 |
| 5,325,851 A | | 7/1994 | Reynolds et al. | 128/207.16 |
| 5,349,950 A | | 9/1994 | Ulrich et al. | 128/207.16 |
| 5,354,267 A | * | 10/1994 | Niermann et al. | 604/32 |
| 5,355,876 A | | 10/1994 | Brodsky et al. | 128/202.27 |
| 5,368,017 A | | 11/1994 | Sorenson et al. | 128/200.26 |
| 5,433,195 A | | 7/1995 | Kee et al. | 128/207.14 |
| 5,460,613 A | | 10/1995 | Ulrich et al. | 604/118 |
| 5,488,949 A | | 2/1996 | Kreifels et al. | 128/207.14 |
| 5,490,503 A | | 2/1996 | Hollister | 128/205.12 |
| 5,513,628 A | | 5/1996 | Coles et al. | 128/200.26 |
| 5,582,165 A | | 12/1996 | Bryan et al. | 128/207.14 |
| 5,598,840 A | | 2/1997 | Iund et al. | 128/207.14 |
| 5,611,336 A | | 3/1997 | Page et al. | 128/207.16 |
| 5,653,231 A | | 8/1997 | Bell | 128/207.16 |
| 5,664,564 A | | 9/1997 | Palmer | 128/205.19 |
| 5,676,136 A | | 10/1997 | Russo | 128/205.24 |
| 5,715,815 A | | 2/1998 | Lorenzen et al. | 128/207.14 |
| 5,730,123 A | | 3/1998 | Lorenzen et al. | 128/207.14 |
| 5,735,271 A | | 4/1998 | Lorenzen et al. | |
| 5,775,325 A | | 7/1998 | Russo | 128/205.12 |
| 5,779,687 A | | 7/1998 | Bell et al. | 604/265 |
| 5,791,337 A | | 8/1998 | Coles et al. | 128/200.26 |
| 5,836,918 A | | 11/1998 | Dondlinger | 604/171 |
| 5,882,348 A | | 3/1999 | Winterton et al. | 604/283 |
| 5,919,174 A | | 7/1999 | Hanson | 604/283 |
| 5,964,223 A | | 10/1999 | Baran | 128/207.14 |
| 6,079,413 A | | 6/2000 | Baran | 128/207.14 |
| 6,109,259 A | | 8/2000 | Fitzgerald | 128/200.26 |
| 6,227,197 B1 | | 5/2001 | Fitzgerald | 128/200.26 |
| D448,842 S | | 10/2001 | Madsen et al. | D24/112 |
| D448,843 S | | 10/2001 | Madsen et al. | D24/112 |
| 6,318,368 B1 | | 11/2001 | Morejon | 128/207.15 |
| 6,526,976 B1 | | 3/2003 | Baran | 128/207.14 |
| 6,575,944 B1 | | 6/2003 | McNary et al. | 604/264 |
| 6,588,425 B2 | | 7/2003 | Rouns et al. | 128/207.14 |
| 6,588,427 B1 | | 7/2003 | Carlsen et al. | 128/207.14 |
| 6,612,304 B1 | * | 9/2003 | Cise et al. | 128/200.26 |
| 7,556,041 B2 | | 7/2009 | Madsen | |
| 2001/0029953 A1 | | 10/2001 | Mattar Neto et al. | 128/207.16 |
| 2001/0044600 A1 | * | 11/2001 | Elkins | 604/119 |

FOREIGN PATENT DOCUMENTS

| | | |
|---|---|---|
| EP | 1210957 | 6/2002 |
| WO | 9317742 | 9/1993 |
| WO | 9531250 | 9/1993 |
| WO | 9514498 | 6/1995 |

* cited by examiner

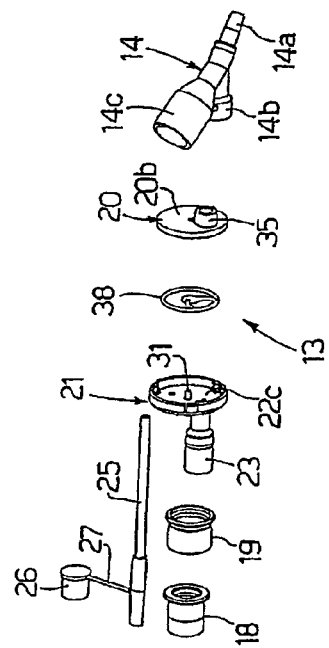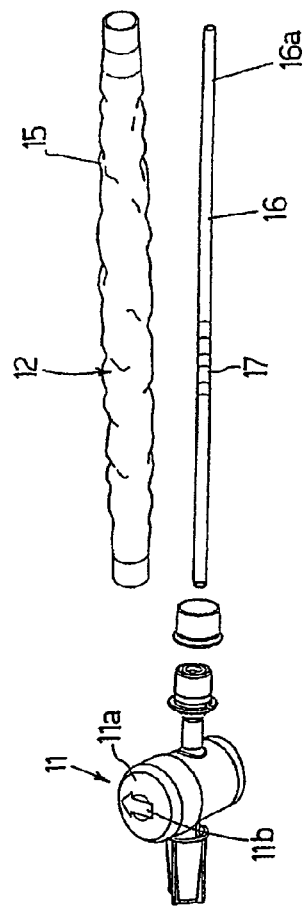
Fig.2

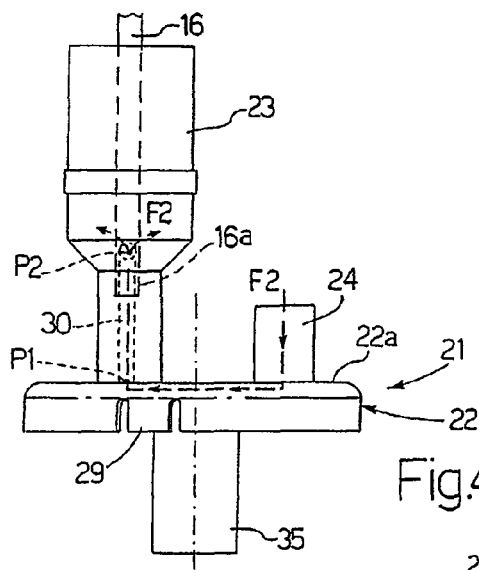
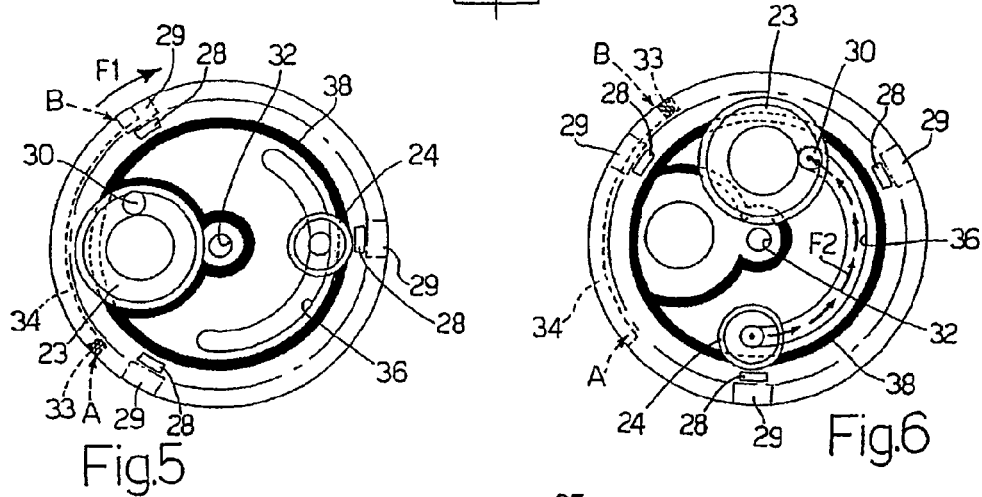
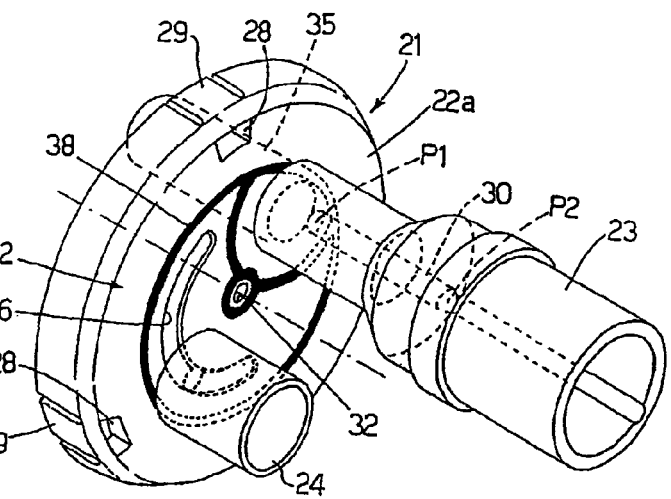

BRONCHOTRACHEAL ACCESS VALVE FOR A BRONCHOASPIRATION APPARATUS

CROSS-REFERENCE TO RELATED APPLICATIONS

This application is a U.S. national stage application of International Application No. PCT/EP2006/005623 filed Jun. 12, 2006, which designates the United States of America, and claims priority to Italian application number B02005A000404 filed Jun. 15, 2005, the contents of which are hereby incorporated by reference in their entirety.

TECHNICAL FIELD

The present invention relates to a bronchotracheal access valve for a bronchoaspiration apparatus.

BACKGROUND

As is known, a bronchoaspiration apparatus, connectable to a ventilation circuit, comprises:
- a vacuum generating and regulating device;
- a catheter body comprising a transparent sleeve and a catheter; and
- a bronchotracheal access valve connected mechanically to a connecting member for connection to a patient's body.

A bronchoaspiration apparatus must ensure complete isolation of the suction catheter from the environment, to prevent contamination of the patient by the environment and vice versa, i.e. contamination of the environment by the patient.

In operation, after a first suction stage, the end portion of the catheter is normally flushed by injecting sterilized water or a saline solution through a passage provided for that purpose.

The flushing operation is potentially hazardous to the patient, particularly in the case of babies. That is, the operator may inadvertently inject the flush fluid without activating the flush fluid suction means; in which case, the flush fluid would flow directly into the patient's trachea, thus resulting in obvious damage, which is particularly serious in the treatment of babies.

SUMMARY

It is therefore a main object of the present invention to provide a bronchotracheal access valve (for a bronchoaspiration apparatus) designed to only permit flushing of the end of the catheter in given patient safety conditions. Consequently, any inadvertent action possibly resulting in flush fluid being injected into the patient's trachea is prevented, even if the bronchotracheal access valve is in the open position.

It is therefore a main object of the present invention to provide a bronchotracheal access valve designed to eliminate the aforementioned drawbacks, and which is intrinsically safe.

According to the present invention, there is provided a bronchotracheal access valve for a bronchoaspiration apparatus, as claimed in the accompanying Claims.

BRIEF DESCRIPTION OF THE DRAWINGS

A non-limiting embodiment of the present invention will be described by way of example with reference to the accompanying drawings, in which:

FIG. 2 shows an exploded three-dimensional assembly drawing of the FIG. 1 bronchoaspiration apparatus;

FIG. 3 shows an enlarged three-dimensional view of a bronchotracheal access valve in accordance with the teachings of the present invention and forming part of the FIGS. 1 and 2 bronchoaspiration apparatus;

FIG. 4 shows a side view of the FIG. 3 bronchotracheal access valve;

FIG. 5 shows a plan view of a first configuration of FIGS. 3 and 4 bronchotracheal access valve;

FIG. 6 shows a plan view of a second configuration of FIGS. 3 and 4 bronchotracheal access valve;

DETAILED DESCRIPTION

Figure 1:
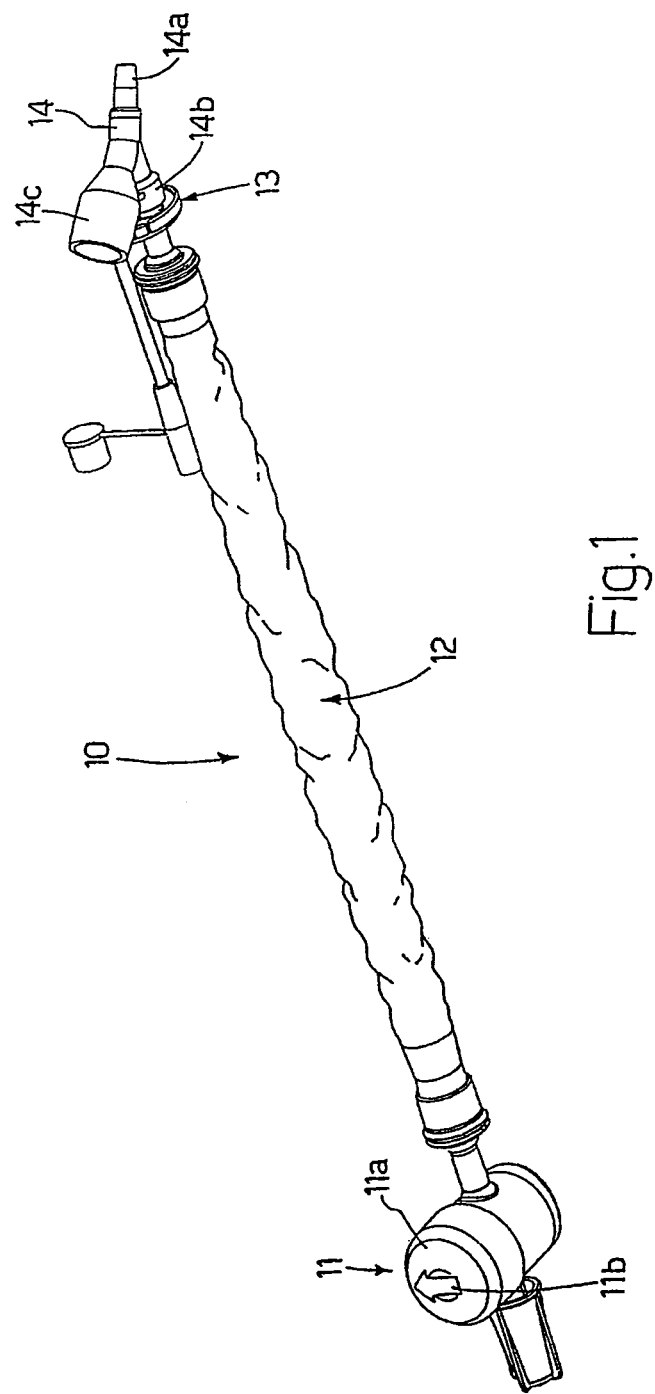
FIG. 1 shows a three-dimensional assembly drawing of a bronchoaspiration apparatus.

Number 10 in FIG. 1 indicates as a whole a bronchoaspiration apparatus connectable to a ventilation circuit (not shown).

Apparatus 10 comprises a vacuum control valve 11 connected mechanically to a catheter body 12.

Apparatus 10 also comprises a bronchotracheal access valve 13 representing the innovative part of apparatus 10 (see below).

A connecting member 14 completes apparatus 10.

More specifically, connecting member 14 comprises a conduit 14a for connection to a patient (not shown); a conduit 14b for connection to bronchotracheal access valve 13; and a conduit 14c for connecting apparatus 10 to a ventilation circuit (not shown).

In the following description, only the details necessary for a clear understanding of the present invention will be described in detail, but those of skill in the art will appreciate that the present invention encompasses variants not specifically discussed in detail herein.

Vacuum control valve 11 and connecting member 14 are known. Therefore, suffice it to say that vacuum control valve 11 comprises a cover 11a marked with an arrow 11b (indicated in the closed position in FIG. 1). When necessary, the operator applies finger pressure on cover 11a and rotates it to set arrow 11b to a vacuum source (not shown) to aspirate bronchial mucus. Only with arrow 11b set to this position, can secretion be aspirated; in any other position of arrow 11b, aspiration is prevented.

As shown in detail in FIG. 2, catheter body 12 comprises a transparent sleeve 15 made of easily deformable, tear-proof plastic material, and which protects a catheter 16 from contamination to and from an external environment. In known manner, catheter 16 comprises a number of depth marks 17 to enable the user to monitor insertion of suction catheter 16 (of minimum 5 Ch size) inside the tracheal/tracheostomic tube.

As shown in FIG. 2, between catheter body 12 and bronchotracheal access valve 13 are inserted a fitting 18 for guiding catheter 16, and a bushing 19 for securing transparent sleeve 15 to fitting 18.

Figure 7:
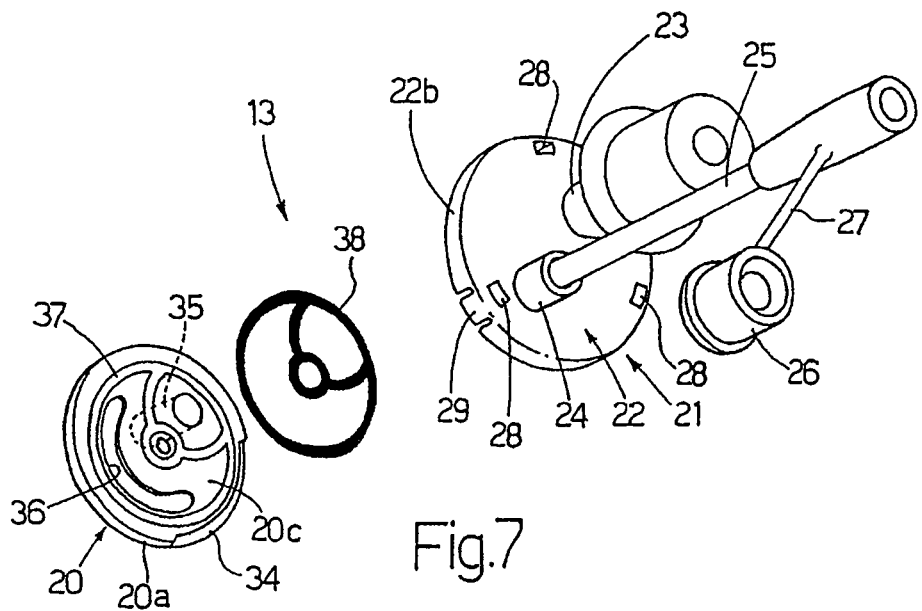
FIG. 7 shows an exploded view of the first configuration of the bronchotracheal access valve in FIG. 5.
Figure 8:
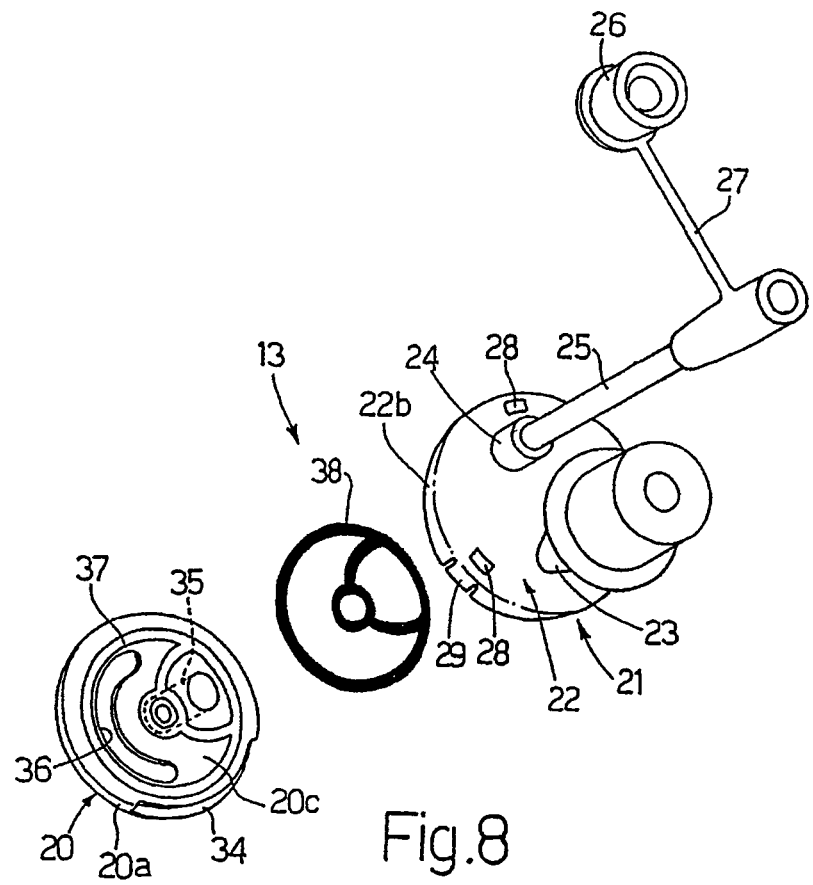
FIG. 8 shows an exploded view of the second configuration of the bronchotracheal access valve in FIG. 6.

As stated, the innovative part is defined by bronchotracheal access valve 13, which is shown in detail in the exploded views in FIGS. 2, 7 and 8.

All the component parts of bronchotracheal access valve 13 are made of transparent plastic material.

With reference to the accompanying drawings, bronchotracheal access valve 13 comprises a substantially disk-shaped first member 20, and a substantially cup-shaped second member 21 (FIGS. 2, 7 and 8).

Second member 21 in turn comprises a cup-shaped main body 22, from a surface 22a (FIG. 4) from which projects a through conduit 23 (e.g. insertion means), for passage of a catheter 16. The through conduit 23 is fixed, in use, to fitting 18 (FIG. 1). A flush conduit 24 (e.g. flush means) projects also from the surface 22a. Conduits 23, 24 are advantageously, though not necessarily, formed in one piece with main body 22.

As shown in FIGS. 1, 2, 7 and 8, a flush tube 25 is inserted inside conduit 24, and has a cap 26 connected to it by a tie 27.

As shown particularly in FIG. 7, main body 22 has 25 three weight-reducing holes 28 located 120° apart, and at each of which a respective tab 29 is formed by conveniently cutting an edge 22b of main body 22.

The function of the three tabs 29 is explained below.

As shown in FIGS. 3, 4, 5 and 6, a channel 30 is integrated in the inner wall of conduit 23, originates at a point P1 at the bottom of conduit 23, and terminates at a point P2 (FIGS. 3, 4).

The functions of channel 30 are explained below, in the section dealing with the operation of bronchotracheal access valve 13.

A surface 22c of main body 22 has a locating pin 31 (FIG. 2) which fits inside a locating hole 32 formed in the centre of first member 20 (FIGS. 5 and 6).

The inner surface of edge 22b has a pin 33, which, in use, engages a guide duct 34 (FIGS. 5, 6, 7 and 8) formed on an edge 20a of first member 20, for the reasons explained in detail below.

For the time being, suffice it to say that pin 33 and guide duct 34 define a stop device.

As shown in FIGS. 2, 3, 4, 7, and 8, a through sleeve 35 (e.g. connecting means) projects from a surface 20b of first member 20, and is connected, in use, to conduit 14b of connecting member 14.

In addition to locating hole 32 and guide duct 34, a surface 20c of first member 20 (FIGS. 7 and 8) also comprises a substantially semicircular duct 36.

Surface 20c also comprises a number of ducts 37 for housing an elastomer seal 38.

Seal 38 obviously provides for hydraulically sealing duct 36 from the mouth of sleeve 35.

That is, seal 38 (e.g., a selective communication means), as will be seen, prevents the flush fluid from accidentally flowing from duct 36 to the mouth of sleeve 35.

During assembly, first member 20, second member 21, and seal 38 (inserted inside ducts 37) are "packed" tightly (FIGS. 7 and 8) together using the deformability of tabs 29 on second member 21, which grip onto edge 20a of first member 20.

In other words, during assembly, main body 22 of second member 21 "clicks" onto first member 20 using the deformability of tabs 29 formed from edge 22b and therefore made of plastic material.

In actual use, second member 21 can be rotated by the operator with respect to first member 20 in the direction indicated by arrow F1 (and about locating pin 31) to move bronchotracheal access valve 13 from a first configuration, shown in FIG. 5, to a second configuration, shown in FIG. 6.

In the first configuration in FIG. 5, pin 33, integral with second member 21, is set to a limit position A along guide duct 34 in first member 20, and conduit 23 is aligned with sleeve 35, with conduit 14b, with fitting 18, and with bushing 19, so that catheter 16 can fit through conduit 23, sleeve 35, and conduit 14b to the desired areas of the patient's body.

In the first configuration in FIG. 5, flush conduit 24 terminates at one end inside duct 36. However, since duct 36 in this configuration does not communicate hydraulically with conduit 23 or channel 30, the flush fluid, even if injected by the operator inadvertently into duct 36 through conduit 24, is also prevented by seal 38 from reaching conduit 23 or channel 30.

To flush an end portion 16a (FIG. 2) of catheter 16, the operator simply withdraws catheter 16 to pull end portion 16a out of sleeve 35 (FIG. 4), and rotates second member 21 with respect to first member 20 in the direction of arrow F1, so that pin 33 is set to a limit position B (FIG. 6) along guide duct 34, and one end of channel 30 is positioned on duct 36. Flush conduit 24 is also rotated in the direction of arrow F1, but a free end of it is still maintained contacting duct 36.

This therefore results in the FIG. 6 configuration, in which, flush fluid injected by the operator into flush conduit 24 flows along duct 36 (arrow F2 in FIGS. 4 and 6) into channel 30 and out at point P2 to flood conduit 23 and so flush end portion 16a of catheter 16. It should be pointed out that, when second member 21 is rotated with respect to first member 20 in the direction of arrow F1, surface 20c of first member 20 (FIGS. 7 and 8) closes the end of conduit 23, thus preventing accidental backflow of the flush fluid from conduit 23 to the patient through sleeve 35 and conduit 14b.

Once flushing is completed, the flush fluid is drained from conduit 23 by known drain systems.

Once end portion 16a is flushed, the operator simply rotates second member 21 with respect to first member 20 in the opposite direction to arrow F1, and then pushes catheter 16 back into sleeve 35 and conduit 14b to continue treatment of the patient.

As will be clear from the foregoing description, the main advantage of the bronchotracheal access valve, which is the main object of the present invention, lies in it being designed to only permit flushing of the end of the catheter in conditions ensuring the utmost safety of the patient.

The invention claimed is:

1. A bronchotracheal access valve for a bronchoaspiration apparatus, the bronchotracheal access valve comprising:
    a first member comprising connecting means for connection to a patient; and
    a second member comprising insertion means by which to insert a catheter into the patient's body, and flush means for flushing an end portion of the catheter;
    a duct formed in the first member and in fluid communication with the flush means, wherein rotation of the second member with respect to the first member is capable of creating selective fluid communication between the flush means and the insertion means via the duct in a flushing configuration, wherein a surface of the first member closes the connecting means to prevent fluid communication between the flush means and the connecting means in the flushing configuration; and
    a seal positioned between the first member and the second member.

2. A valve according to claim 1, wherein the duct is substantially semicircular.

3. A valve according to claim 1, wherein the duct comprises a channel integrated in an inner wall of the insertion means.

4. A valve according to claim 1, wherein in a valve open configuration the flush means is sealed by the seal.

5. A valve according to claim 1, further comprising a stop device.

6. A valve according to claim 1, wherein the first member comprises a number of ducts for housing the seal.

7. A valve according to claim 1, wherein the seal is made of elastomer.

8. A valve for a bronchoaspiration apparatus, the valve comprising:
    a patient connection conduit for connection to a patient;

and an adjustable valve member coupled to a catheter insertion conduit and a flush conduit and comprising first and second members;
wherein the second member is capable of being rotated with respect to the first member to switch between:
 a first position in which the catheter insertion conduit is communicatively coupled to the flush conduit but not the patient connection conduit;
 and a second position in which the catheter insertion conduit is communicatively coupled to the patient connection conduit but not to the flush conduit;
 and wherein the valve member comprises a seal disposed between the first and second members and having a first region that seals a duct in communication with the flush conduit from the patient connection conduit in the second position and that seals the flush conduit and the catheter insertion conduit in fluid communication with one another from the patient connection conduit in the first position.

9. A valve according to claim 8, wherein:
the valve first member at least partially defines the duct;
in the second position, the catheter insertion conduit and the flush conduit are positioned such that the duct cannot communicate fluid between the catheter insertion conduit and the flush conduit;
and in the first position, the catheter insertion conduit and the flush conduit are positioned such that the duct can communicate fluid between the catheter insertion conduit and the flush conduit.

10. A valve according to claim 9, wherein the duct is substantially semicircular.

11. A valve according to claim 8, wherein the patient connection conduit is coupled to the first member.

12. A bronchoaspiration apparatus, comprising:
a vacuum control system;
a catheter body including a sleeve and a catheter;
a patient connection conduit for connection to a patient;
 and a valve including:
  a first valve member coupled to a catheter insertion conduit and a flush conduit;
  and a second valve member associated with the patient connection conduit, wherein a position of the second valve member with respect to the first valve member is adjustable between:
   a first position in which the catheter insertion conduit is communicatively coupled to the flush conduit but not the patient connection conduit, such that fluid may be delivered from the flush conduit to the catheter insertion conduit;
   and a second position in which the catheter insertion conduit is communicatively coupled to the patient connection conduit but not to the flush conduit, such that the catheter may be inserted through the catheter insertion conduit and the patient connection conduit;
 a duct formed in the second valve member and in fluid communication with the flush conduit capable of creating selective fluid communication between the flush conduit and the insertion conduit via the duct in the first position, wherein a surface of the first member closes the connecting means to prevent fluid communication between the flush means and the connecting means in the flushing configuration; and
 and wherein a seal is disposed between the first and second valve members.

13. An apparatus according to claim 12, wherein:
in the second position of the first valve member, the catheter insertion conduit and the flush conduit are positioned such that the duct cannot communicate fluid between the catheter insertion conduit and the flush conduit;
and in the first position of the first valve member, the catheter insertion conduit and the flush conduit are positioned such that the duct can communicate fluid between the catheter insertion conduit and the flush conduit.

14. An apparatus according to claim 12, wherein the first valve member is rotatable relative to the second valve member in order to adjust the first valve member between the first and second positions.

15. An apparatus according to claim 12, wherein:
the duct comprises an elongated curved duct;
and the flush conduit includes an opening that moves along the elongated curved duct as the first valve member is adjusted.

* * * * *